United States Patent [19]
Bauer et al.

[11] Patent Number: 5,750,678
[45] Date of Patent: May 12, 1998

[54] WATER-SOLUBLE DEXTRAN FATTY ACID ESTERS AND THEIR USE AS SOLUBILIZERS

[75] Inventors: Kurt H. Bauer, Im Finkeler 4, D-79112 Freiburg; Thomas Reinhart, Gundelfingen, both of Germany

[73] Assignee: Kurt H. Bauer, Freiburg, Germany

[21] Appl. No.: 648,038

[22] PCT Filed: Sep. 14, 1995

[86] PCT No.: PCT/EP95/03625

§ 371 Date: Aug. 30, 1996

§ 102(e) Date: Aug. 30, 1996

[87] PCT Pub. No.: WO96/08517

PCT Pub. Date: Mar. 21, 1996

[30] Foreign Application Priority Data

Sep. 16, 1994 [DE] Germany ............... 44 33 101.0

[51] Int. Cl.$^6$ ............. C08B 37/16; C08B 37/02; C07G 17/00; C12P 7/40
[52] U.S. Cl. ............. 536/103; 536/124; 536/112; 536/104; 435/136; 435/135; 435/134; 562/887; 562/405; 562/400; 560/1; 560/2; 560/5; 252/351
[58] Field of Search ............. 536/103, 124, 536/112, 104; 514/786, 785; 424/484; 435/136, 135, 134; 562/887, 405, 400; 560/1, 2, 5; 252/351

[56] References Cited

U.S. PATENT DOCUMENTS

| | | | |
|---|---|---|---|
| 5,264,460 | 11/1993 | Jakobson et al. | 514/786 |
| 5,576,012 | 11/1996 | Bauen et al. | 424/422 |

FOREIGN PATENT DOCUMENTS

| | | |
|---|---|---|
| 0094692 | 11/1983 | European Pat. Off. |
| 4136324 | 5/1993 | Germany |

OTHER PUBLICATIONS

Die Pharmazie, vol. 50, No. 6, Jun. 1995 DE, pp. 403–407, T. Reinhart, et al. "Untersuchungen zum Hämolyse– und ...".

Chemical Abstracts, vol. 79, No. 16, 22 Oct. 1973, Columbus, OH, US; abstract No. 93706d.

Primary Examiner—Louise Leary
Attorney, Agent, or Firm—Sughrue, Mion, Zinn, Macpeak & Seas, PLLC

[57] ABSTRACT

The invention relates to a water-soluble, haemolytically inactive dextran fatty carboxylate with amphiphilic properties made from a dextran with an average molecular weight of 5,000 to 100,000 and a $C_{10}$ to $C_{14}$ fatty acid, preferably a $C_{12}$ fatty acid, wherein the average degree of substitution is between 0.005 and 0.15 and is adjusted, depending on the average molecular weight of the dextran fatty carboxylate and the chain-length of the fatty acid used, in such a way that the dextran fatty carboxylate is soluble in water at room temperature, a process for its preparation and pharmaceutical or cosmetic preparations which contain it as solubilizer.

12 Claims, 1 Drawing Sheet

Solubilisation of diazepam by lauroyl dextraneS

Solubilisation of diazepam by lauroyl dextranes

WATER-SOLUBLE DEXTRAN FATTY ACID ESTERS AND THEIR USE AS SOLUBILIZERS

The invention relates to water-soluble dextran fatty carboxylates, a process for their preparation and their use as solubilizers for pharmaceutical or cosmetic active substances which are sparingly soluble in water. The dextran fatty carboxylates according to the invention are macromolecular surfactants which, surprisingly, in contrast to most low molecular weight surfactants have no haemolyzing properties and which therefore enable the formulation and production of pharmaceutical and cosmetic preparations which are better tolerated.

Pharmaceutical and cosmetic active substances are not always sufficiently soluble in water. Inadequate water solubility of active substances means that homogeneous preparations with an acceptable appearance cannot be obtained and also that in many cases the effect being striven for cannot be achieved to the optimum extent. This type of active substance, therefore, has to be solubilized with amphiphilic agents, eg surfactants. Not only the appearance but also the bioavailability and the efficacy are improved by this means and in this way. The bioavailability of the active substance also depends on the conditions prevailing at the site of re-sorption in the patient, such as the degree of fullness of the stomach and digestive tract and on peristalsis. In the case of topically applied transdermal and cosmetic preparations, analogous problems also occur during penetration or permeation of the active substance in the parts of the skin or mucous membrane involved, these being associated with the ability to disperse and with diffusion properties. Unsatisfactory dissolution of the active substance also produces non-uniform distribution and thus a non-uniform effect.

In WO 92/10211 pharmaceutical preparations are described which contain sparingly soluble active substances and which are intended for intravenous application. To solubilize the sparingly soluble active substance a polymer is used which consists of three parts A, B and C. Preparation of the polymer requires several steps, which is a disadvantage.

Preparations made from pure dextran, hydroxyethyl starch or other suitable polymers are used as plasma expanders in hypovolemic conditions, ie. they are assumed to be pharmacologically harmless. Dextran 60 with an average molecular weight of 60,000 (varying between 25,000 and 110,000) and dextran 40 with an average molecular weight of 40,000 (varying between 15,000 and 70,000) are used as 6% or 10% strength solutions. Dextran 40 is capable of improving microcirculation. Aggregates of erythrocytes and thrombocytes are broken up and the viscosity of the blood is lowered.

Dextran 40 has a half-life in blood of about 6 hours, dextran 60 has a half-life of more than 24 hours. The upper threshold for the ability of dextran to pass through or be present in the kidneys is located at a relative molecular weight of about 50,000. Thus dextrans are largely eliminated via the kidney. The proportion remaining in the body is slowly and completely degraded by endogenous enzymes to produce water and carbon dioxide. Tolerance to dextrans is good.

Dextran esters of a variety of fatty acids ($C_4$ to $C_{18}$) have been known for some time. However, up to the present only water-insoluble products have been described on the whole. At the moment there are still no satisfactory systems known by means of which sparingly soluble drugs or sparingly soluble cosmetic agents can be converted into a form which is suitable for use in humans or animals. Thus, in particular, sparingly soluble pharmaceutical active substances cannot be converted into a form which is suitable for parenteral or oral or dermal or trans-dermal application, or only with great difficulty.

The present invention is based on the object of providing surfactants which have the property of solubilizing cosmetic and pharmaceutical active substances which are sparingly soluble or insoluble in water or in a physiological substrate.

According to the invention, oligomeric or polymeric surfactants will be provided which are characterized by a lack of in vivo haemolysis activity, can be administered parenterally, orally, or even topically, have no side effects, in particular no side effects which are provoked by possible interaction between surfactants and blood cell membranes or surfactants and membranes in the gastro-intestinal tract. The polymeric surfactants will be able to gain access to the kidneys relatively easily. Oligomeric surfactants can pass through the kidney because of their low molecular weight.

Furthermore, a method for preparing the surfactants and their use will be provided.

According to the invention, pharmaceutical and cosmetic preparations will be made available which contain active substances which are sparingly soluble in water and which can be formulated in such a way that the active substance is homogeneously dispersed and is available in sufficient amounts for absorption and distribution in an organism. The solubility of drugs or cosmetic active substances in water is important for two reasons. Firstly because of the toxicity of many non-aqueous solvents and secondly for environmental reasons. For these reasons water is by far the most important solvent for medical and cosmetic preparations. In order for resorption to take place, drugs must dissolve in both hydrophilic, physiological fluids and also in lipophilic membranes to an equilibrated extent. From experience, drugs which are less than 1% soluble in aqueous media can produce bioavailability problems. Therefore it is important that sparingly soluble or insoluble active substances are present in their forms of administration in a dissolved or solubilized form, as a molecular dispersion or at least as a colloidal dispersion.

The pharmaceutical and cosmetic preparations according to the invention are intended to be stable and also to form no harmful degradation products when stored for a long time. It is intended in particular to provide pharmaceutical preparations which are suitable for oral and parenteral administration.

The invention provides water-soluble, haemolytically non-active dextran fatty carboxylates with amphiphilic properties made from a dextran with an average molecular weight of 5,000 to 100,000 and a $C_{10}$ to $C_{14}$ fatty acid, preferably a $C_{12}$ fatty acid, wherein the average degree of substitution is between 0.005 and 0.15 and is adjusted, depending on the average molecular weight of the dextran fatty carboxylate and the chain length of the fatty acid used, in such a way that the dextran fatty carboxylate is soluble in water at room temperature.

The invention also provides a process for preparing water-soluble dextran fatty carboxylates according to one of claims 1 to 4, which is characterized in that a) dextran with an average molecular weight of 5,000 to 100,000 is dissolved in a solvent mixture of formamide and N-methylpyrrolidone, a $C_{10}$ to $C_{14}$ fatty acid halide is added dropwise in an amount such that the final product has an average degree of substitution between 0.005 and 0.15, the unreacted fatty acid is washed out with a low molecular weight aliphatic alcohol in which the product does not dissolve, and the dextran fatty carboxylate is then recovered by aqueous extraction, or b) dextran with an average molecular weight of 5,000 to 100,000 is dissolved in dimethyl sulphoxide, a $C_{10}$ to $C_{14}$ fatty acid halide is added dropwise to the solution in an amount such that the dextran fatty carboxylate has a degree of esterification between 0.005 and 0.15, and the dextran fatty carboxylate is isolated in a manner known per se.

The invention also relates to a pharmaceutical or cosmetic preparation which contains one or more pharmaceutical or cosmetic active substances which are sparingly soluble in water, in solubilized form, and a surfactant as solubilizer, which is characterized in that this surfactant (solubilizer) is a water-soluble dextran fatty carboxylate as described above.

Dextran fatty carboxylates according to the invention have the surprising property that they solubilize pharmaceutical or cosmetic active substances which are sparingly soluble in water. Surprisingly, it was found that the requirements mentioned above can be satisfied using dextran fatty carboxylates according to the invention. The dextran fatty carboxylates according to the invention, and thus the pharmaceutical or cosmetic preparations prepared therefrom, surprisingly, exhibit no haemolysis, in contrast to most of the surfactants used in the past. This has the advantage that preparations according to the invention have fewer side effects triggered by haemolysis than do known products.

To prepare water-soluble dextran fatty carboxylates according to the invention, oligomeric or polymeric dextran with an average molecular weight between 5,000 and 100,000, preferably between 8,000 and 70,000, in particular between 10,000 and 40,000 are used. It is particularly preferred that a dextran with a relative molecular weight between 10,000 and 40,000 be used because these dextrans have molecular dimensions which definitely produce no haemolysis, but are also not too large to pass through the kidneys in their undegraded form. The dextrans used are polymers which never contain a precisely defined substance. They are generally statistical mixtures of a main compound, with values for the molecular weight scattered statistically around an average value. This type of dextran can be obtained commercially. These dextrans are esterified with a $C_{10}$ to $C_{14}$ fatty acid, preferably a $C_{12}$ fatty acid. Examples of the fatty acids mentioned are n-decanoic acid (capric acid), n-dodecanoic acid (lauric acid) and myristic acid, wherein lauric acid is preferred.

Dextran fatty carboxylates are synthesized using a reaction which is analogous to one used to produce some polymers. In this case a $C_{10}$ to $C_{14}$ fatty acid, for example lauric acid, is grafted onto dextran with the selected molecular weight.

When preparing dextran fatty carboxylates the solvent plays an essential part. Only a few solvents, such as eg. dimethyl sulphoxide or formamide, are able to dissolve both reaction partners and thus enable reaction in a homogeneous medium. It is possible to synthesize dextran fatty carboxylates in heterogeneous media, but this generally leads to sparingly water-soluble products because the reaction is difficult to control in heterogeneous media. In order to achieve uniform esterification over all the dextran molecules which are present, the reaction is preferably performed in a mixture of formamide and N-methylpyrrolidone, for example 1:8 vol/vol. Formamide or N-methylpyrrolidone may also be used on their own. The reactants are soluble both in formamide and also in the formamide/N-methylpyrrolidone mixture so that statistical distribution of the substituents over all the dextran molecules takes place.

By way of example, the dextran, preferably dextran 20, is dissolved in formamide. N-methylpyrrolidone is added and then the fatty acid chloride is added dropwise. Addition is performed dropwise in such a way that the temperature of the reaction mixture does not exceed 400° C. This can be achieved either by regulating the rate of addition of the drops or by external cooling. Water is excluded from the process. The product obtained is purified by washing with a low molecular weight aliphatic alcohol, eg isopropanol, which removes unreacted fatty acid. In the next purification stage the non-water-soluble reaction components are filtered off using an aqueous extraction step. Furthermore, the final product may be dialyzed to remove residues of the solvent used, this being difficult to distil off, then filtered sterile and freeze dried.

In order for the dextran fatty carboxylates according to the invention to be water-soluble, the degree of substitution must be selected as a function of the molecular weight of the dextran used as starting material and the chain length of the fatty acid used. The higher the molecular weight, the lower must the degree of substitution be for the product obtained to be water-soluble. In the case of low molecular weights the degree of substitution is at the upper end of the range and in the case of high molecular weights it is at the lower end of the range. The degree of substitution of the dextran fatty carboxylates according to the invention is in the range between 0.005 and 0.1, preferably in the range between 0.01 and 0.1. As specified above in connection with the molecular weight, the degree of substitution is also a statistical value.

The degree of substitution of the dextran fatty carboxylates is determined in a conventional manner. The dextran fatty carboxylates are hydrolysed in an alkaline solution, then the fatty acid released is converted into the methyl ester of the fatty acid by methylation in methanol in the presence of a boron trifluoride/methanol complex as catalyst. The concentration of the methyl ester of the fatty acid is determined quantitatively by gas chromatography. After evaluating the peak areas the degree of substitution DS is produced by the following formula I $$DS = \frac{Mol_{FS} \cdot 162,14}{(Mass_{PO} - MG_{FS} \cdot Mol_{FS}) \cdot 1 + \frac{Mol_{FS}}{MG_{FS} \cdot Mol_{FS}} \cdot MG_H} \quad \text{I}$$

wherein the parameters in the equation are defined as follows:

$Mol_{FS}$=moles of fatty acid substituent
$Mass_{PO}$=initial weight of polymer
$MG_{FS}$=molecular weight of fatty acid substituents
$MG_H$=atomic weight of hydrogen.

The pharmaceutical preparation according to the invention contains a pharmaceutical or cosmetic active substance whose solubility in distilled water is less than 1 in 100. The concentration of active substance in the preparation according to the invention may vary greatly and depends on the requisite therapeutic dose in which the active substance is to be administered. This can easily be determined by a person skilled in the art by appropriate routine tests. Problems arise in the development of the formulation of a drug preparation if the solubility of the active substance involved is lower than the therapeutic dose required. An active substance then has to be solubilized with the assistance of, or the addition of, a surfactant. This surfactant must have suitable solubilizing properties or an adequate solubilizing capacity for the active substance. Surprisingly, it has been shown that dextran fatty carboxylates according to the invention have a solubilizing effect on active substances which are sparingly soluble in water.

Particularly suitable water-insoluble pharmaceutical and/or cosmetic active substances for this purpose are diazepam and other benzodiazepines
nifedipine and other dihydropyridines
ciprofloxacin and other quinolones
cyclosporin and derivatives
fat-soluble vitamins
fatty acids and their derivatives
antifungal agents, eg nystatin, griseofulvin, clotrimazole, ketoconazole and other imidazole antifungal agents
sun protection agents or light filters, eg UV-A and UV-B filters with affinities for the epithelial layer of the skin, such as ethylhexyl-p-methoxycinnamate, octyl p-cinammates, homomenthyl salicylate, 2-hydroxy-4-methoxybenzophenone, 2-ethylhexyl-4-dimethylaminobenzoate and similar derivatives sold under trade names like Eusolex®, Uvinol®, Novantisol®, Padimate®, Escalol®, Neo-heliopan® and Parsol®.

The preparation according to the invention may be presented in a form suitable for oral, parenteral, topical, rectal or intra-vaginal administration for humans or animals. For example, the preparation may be placed in hard or soft gelatine capsules and administered orally. The preparation may also be presented in a solid, semi-solid or liquid form. It may optionally be diluted with pharmaceutically or cosmetically acceptable solvents and/or diluents. Examples of pharmaceutically acceptable solvents and/or diluents are water, alcohols and polyethylene glycols.

The pharmaceutical or cosmetic preparations according to the invention may contain additional pharmaceutically or cosmetically acceptable auxiliary agents and/or diluents. Auxiliary agents which may be particularly mentioned are co-solvents, stabilizers and preservatives.

Using the model substance diazepam, the solubilization capacity of the surfactants is determined and compared with the data in the literature relating to other surfactants. The physico-chemical properties of the active substance determine the site of solubilization within a micelle. Diazepam is solubilized in the area of the lipophilic side chains.

Appropriate solubilizing properties or solubilising capacities are determined by measuring the saturation concentration of a substance (solubilizate) in a range of different concentrations of surfactant solutions. To evaluate the results, the saturation concentration of the solubilizate is plotted against the concentration of surfactant. The solubilization tests are mainly performed using the "shaking method", because in this case the saturation solubilities are reached more rapidly.

The units for solubilization capacity k are moles of solubilizate per mole of surfactant or milligrams of solubilizate per milligram of surfactant.

In solubilization tests, the "shaking method" is mainly utilised because here the saturation solubility is reached more rapidly.

To determine the saturation solubility by the "shaking method", excess diazepam is added to surfactant solutions of different concentrations. These suspensions are shaken for about 200 hours at 25° C. in a constant temperature shaking waterbath. Before the saturation solubilities are determined by UV measurements, excess diazepam is filtered off.

Figure 1:
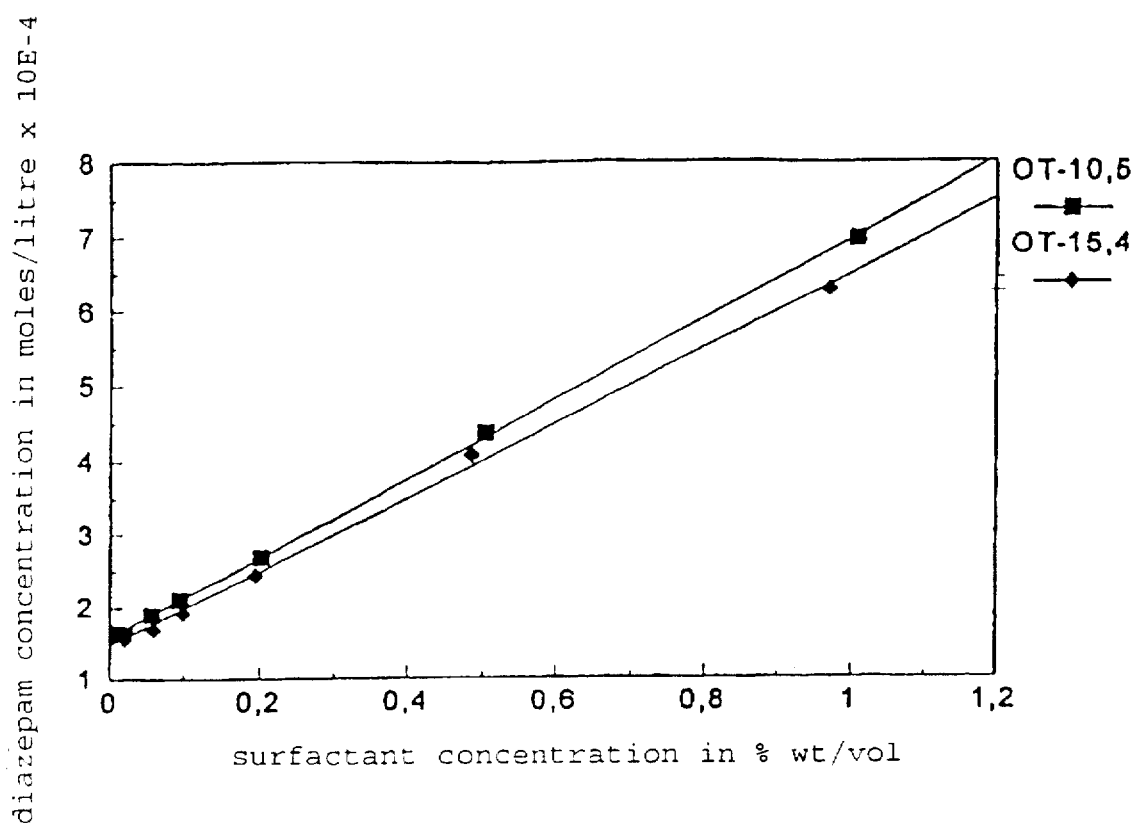
FIG. 1 gives the solubility promotion (solubilization) of diazepam due to lauroyl dextran. The solubilization capacity is determined in each case from the gradient of the straight line. The region over which the curve is a straight line in the case of the hydrophilic surfactants which are important for our purposes extends up to about 5% at low surfactant concentrations. Much higher concentrations of active substance dissolve in these relatively low concentration surfactant solutions, as compared with surfactant-free water, so the solubilization effects are clearly recognizable.

Table 1 gives a comparison of a few solubilization capacities. The solubilization capacities of the new oligomeric surfactants OT 10.5 and 15.4 are comparable with those of commercially available low molecular weight polyethylene glycol-660-monohydroxystearate (Solutol HS 15). The solubilization capacity of polyoxyethylene/polyoxypropylene copolymer (Pluronic F68) however is about ten times weaker.

TABLE 1

| Surfactant | k |
| --- | --- |
| A) low mol wt surfactants: | |
| Pluronic F 68 | 0.0013 |
| Solutol HS 15 | 0.0179 |
| B) new oligomeric surfactants according to the invention: | |
| OT 10.5 | 0.0154 |
| OT 15.4 | 0.0143 |

OT 10.5 represents an oligomeric surfactant (dextran fatty carboxylate) in which the average degree of substitution is such that, statistically, there is one fatty acid to 10.5 glucose units. Table 1 shows that the solubilization capacities of the new oligomeric surfactants are comparable to that of the best low molecular weight surfactants. They are, however, less haemolytic.

Haemolysis tests show that dextran fatty carboxylates according to the invention have lower haemolytic activity than low molecular weight surfactants. This is of great importance for practical application.

The following examples illustrate the invention.

EXAMPLE 1

Preparation of Lauroyl Dextran (DS 0.1)

In an apparatus consisting of a round-bottomed flask, magnetic stirrer and a waterbath, 6.0 g of dextran 250.000, obtained in a biological reaction using Leuconostoc ssp. and then dried, are dissolved in 100 ml of dry formamide. After the addition of 80 ml of anhydrous N-methylpyrrolidone the solution is heated to 45° C. and 8.0 g of lauric chloride are gradually added dropwise, with stirring. The solution is then stirred for a further 48 hours at 45° C.

After cooling to room temperature, 5 ml of water are added to decompose excess acid chloride. The solvent mixture is concentrated under vacuum. After decanting the lauric acid produced, the solid crude product is finely dispersed in isopropanol and stirred for 12 hours. Lauroyl dextran (DS 0.1) is not soluble in isopropanol. To remove the lauric acid present, therefore, the mixture is washed three more times with isopropanol. The resulting ester is dissolved in water and dialysed for 3 days in order to remove low molecular weight esters. After sterile filtration the product is freeze dried and stored over phosphorus pentoxide.

The product is a white solid substance which looks like wadding. Aqueous solutions foam strongly.

EXAMPLE 2

Preparation of Dodecanoyl Dextran 4 g of dextran with a relative molecular weight of 146.000 are dissolved in 80.0 g of dimethyl sulphoxide. After the addition of 9.0 g of dodecanoic chloride, stirring is continued.

To decompose excess acid chloride, 10 ml of water are added and the solvent mixture is concentrated under vacuum. After decanting the dodecanoic acid produced, the solid crude product is finely dispersed in isopropanol and stirred for 12 hours. Centrifuged dodecanoyl dextran is then washed three times with isopropanol. This product is filtered as a 1% strength aqueous solution and dialysed. After sterile filtration the product is freeze dried and stored over phosphorus pentoxide.

The degree of substitution DS is between 0.2 and 0.3. The product is a white solid substance which looks like wadding. Aqueous solutions foam.

EXAMPLE 3

Preparation of Myristoyl Dextran 3.0 g of dextran with a relative molecular weight of 60.000 are dissolved in 60.0 g of dry formamide. After the addition of 7.0 g of myristic chloride, stirring is continued.

To decompose excess acid chloride, 10 ml of water are added and the solvent mixture is concentrated under vacuum. After decanting off the myristic acid produced, the solid crude product is finely dispersed in isopropanol and stirred for 12 hours. The isolated dextran carboxylate is washed three more times with isopropanol. This product is filtered, dialysed and freeze dried.

The degree of substitution DS is 0.1 to 0.2. The product is a solid substance which looks like wadding.

EXAMPLE 4

Preparation of Palmitoyl Dextran 2.0 g of dextran with a relative molecular weight of 100.000 are dispersed in 120 ml of N-methylpyrrolidone. After the addition of 6.0 g of palmitic chloride, stirring is continued. To decompose excess acid chloride, 15 ml of water are added. Then the solvent is removed under vacuum. After decanting off the palmitic acid produced the solid crude product is finely dispersed in isopropanol and stirred. The isolated dextran fatty carboxylate is then washed three more times with isopropanol. This product is dialyzed and freeze dried.

The degree of substitution DS is between 0.3 and 0.4. The product is a solid substance which looks like wadding. It is sparingly soluble and therefore suitable as an embedding material.

Examples of Formulations for Pharmaceutical and Cosmetic Preparations

Formulation Example 1

Diazepam Ampoules

To a mixture of 1858.0 mg of Aqua for injection, 2.0 mg of sodium disulphite and 30 mg of benzyl alcohol as preservative, are added 100.0 mg of lauroyl dextran (DS 0.1), prepared in accordance with example 1, and 10.0 mg of diazepam, and the mixture is then carefully stirred, until a clear solution is produced. This solution is transferred to a 2 ml ampoule in a manner known per se.

Formulation Example 2

Aqueous Vitamin A Eye Drops

To a mixture of 929.0 mg of Aqua for injection, 1.0 mg of the disodium salt of EDTA and 20 ml of chlorobutanol as preservative, are added 50.0 mg of dodecanoyl dextran (DS 0.1), prepared in accordance with example 2, and 1000 I.U. of retinol palmitate (vitamin A). The mixture is carefully stirred until a clear solution is produced. This solution is transferred to an ophthiole (1 ml) or an eyedropper in a manner known per se.

Formulation Example 3

Sun Protection Agent

To a mixture of 62.5 g of Aqua purificata and 10.0 g of glycerol are added 25.0 g of lauroyl dextran (DS 0.1), prepared in accordance with example 1, and 2.5 g of the sun protection agent Eusolex. This is carefully stirred until a solution is produced. This solution is transferred to plastic bottles (100 ml) by a method known per se.

We claim:

1. A water-soluble, hemolytically inactive dextran fatty carboxylate with amphiphilic properties made from a dextran with an average molecular weight of 5,000 to 100,000 and a $C_{10}$ to $C_{14}$ fatty acid, wherein the average degree of substitution is between 0.005 and 0.15 and is adjusted, depending on the average molecular weight of the dextran fatty carboxylate and the chain-length of the fatty acid used, in such a way that the dextran fatty carboxylate is soluble in water at room temperature.

2. The water-soluble dextran fatty carboxylate according to claim 1, characterised in that the average molecular weight of the dextran is 10,000 to 40,000.

3. The water-soluble dextran fatty carboxylate according to claims 1 or 2, wherein the ester is a $C_{12}$ fatty acid.

4. The water-soluble dextran fatty carboxylate according to at least one of claims 1 or 2, wherein the degree of esterification is between 0.005 and 0.15.

5. The process for preparing the water-soluble dextran fatty carboxylate according to one of claims 1 or 2 wherein (a) dextran with an average molecular weight of 5,000 to 100,000 is dissolved in a solvent mixture of formamide and N-methylpyrrolidone, a $C_{10}$ to $C_{14}$ fatty acid halide is added dropwise in an amount such that the final product has an average degree of substitution between 0.005 and 0.15, the unreacted fatty acid is washed out with a low molecular weight aliphatic alcohol in which the product does not dissolve, and the dextran fatty carboxylate is then obtained by aqueous extraction, or (b) dextran with an average molecular weight of 5,000 to 100,000 is dissolved in dimethyl sulphoxide, $C_{10}$ to $C_{14}$ fatty acid halide is added dropwise to the solution in an amount such that the dextran fatty carboxylate has a degree of esterification between 0.005 and 0.15, and the dextran fatty carboxylate obtained is isolated.

6. The process according to claim 5 wherein the dextran fatty carboxylate is finally purified by dialysis in order to remove high-boiling residues of the solvent used, filtered sterile and freeze dried.

7. The process according to claim 5 or 6, wherein the $C_{10}$ to $C_{14}$ fatty acid halide is added at such a rate that the temperature of the reaction mixture does not rise above 40° C., or that the reaction mixture is cooled.

8. A pharmaceutical or cosmetic preparation which contains one or more pharmaceutical or cosmetic active substances which are sparingly soluble in water, in solubilized form, and a surfactant as solubilizer, wherein this surfactant (solubilizer) is a water-soluble dextran fatty carboxylate according to one of claims 1 or 2.

9. The pharmaceutical preparation according to claim 8 containing as a pharmaceutical active substance, diazepam or other benzodiazepines, nifedipine or other dihydropyridines, ciprofloxacin or other quinolones, cyclosporin or its derivatives.

10. The cosmetic preparation according to claim 8, containing as a cosmetic active substance, a fat-soluble vitamin, a fatty acid or a fatty acid derivative, an antifungal agent, a light protective substance or mixtures of these substances.

11. The water-soluble, hemolytically inactive dextran fatty carboxylate according to claim 1 wherein the $C_{10}$ to $C_{14}$ fatty acid is a $C_{12}$ fatty acid.

12. The water-soluble dextran fatty carboxylate according to claim 1 in a pharmaceutical or cosmetic preparation.

* * * * *